US011359017B2

(12) United States Patent
Fujimura

(10) Patent No.: US 11,359,017 B2
(45) Date of Patent: Jun. 14, 2022

(54) METHOD OF ALTERING AN ANTIBODY-RELATED ADVERSE EVENT BASED ON SCD163 AND/OR CXCL5 LEVELS

(71) Applicant: TOHOKU UNIVERSITY, Miyagi (JP)

(72) Inventor: Taku Fujimura, Miyagi-ken (JP)

(73) Assignee: TOHOKU UNIVERSITY, Miyagi (JP)

( * ) Notice: Subject to any disclaimer, the term of this patent is extended or adjusted under 35 U.S.C. 154(b) by 567 days.

(21) Appl. No.: 16/314,474

(22) PCT Filed: Jun. 30, 2017

(86) PCT No.: PCT/JP2017/024244
§ 371 (c)(1),
(2) Date: Dec. 31, 2018

(87) PCT Pub. No.: WO2018/003995
PCT Pub. Date: Jan. 4, 2018

(65) Prior Publication Data
US 2019/0202915 A1    Jul. 4, 2019

(30) Foreign Application Priority Data

Jul. 1, 2016 (JP) .............................. JP2016-131913

(51) Int. Cl.
| | |
|---|---|
| *G01N 33/68* | (2006.01) |
| *G01N 33/50* | (2006.01) |
| *G01N 33/15* | (2006.01) |
| *C07K 16/28* | (2006.01) |
| *G01N 33/53* | (2006.01) |
| *C07K 16/24* | (2006.01) |
| *A61P 35/00* | (2006.01) |
| *C07K 14/52* | (2006.01) |
| *C07K 14/705* | (2006.01) |
| *A61K 39/00* | (2006.01) |

(52) U.S. Cl.
CPC .......... *C07K 16/2818* (2013.01); *A61P 35/00* (2018.01); *C07K 14/52* (2013.01); *C07K 14/705* (2013.01); *C07K 16/24* (2013.01); *C07K 16/2827* (2013.01); *G01N 33/15* (2013.01); *G01N 33/50* (2013.01); *G01N 33/5008* (2013.01); *G01N 33/53* (2013.01); *G01N 33/68* (2013.01); *G01N 33/6893* (2013.01); *A61K 2039/505* (2013.01); *G01N 2333/522* (2013.01); *G01N 2333/70596* (2013.01); *G01N 2800/52* (2013.01)

(58) Field of Classification Search
CPC .............. C07K 16/2818; G01N 33/15; G01N 33/5008; G01N 33/6893; G01N 2333/522; G01N 2333/70596; G01N 2800/52; A61P 35/00
See application file for complete search history.

(56) References Cited

U.S. PATENT DOCUMENTS

| 10,034,938 B2 | 7/2018 | Vanderwalde et al. |
| 2004/0054144 A1 | 3/2004 | Itai |
| 2015/0118245 A1 | 4/2015 | Weber et al. |
| 2017/0145099 A1 | 5/2017 | Ito et al. |

FOREIGN PATENT DOCUMENTS

| EP | 2 937 698 | 10/2015 |
| JP | 2015-526525 | 9/2015 |
| JP | 2016-64989 | 4/2016 |
| WO | 02/40990 | 5/2002 |
| WO | 2015/036499 | 3/2015 |
| WO | 2015/190538 | 12/2015 |
| WO | 2016/081947 | 5/2016 |
| WO | 2016/100975 | 6/2016 |

OTHER PUBLICATIONS

Pickens SR, et al. (Dec. 2011) Angiogenesis. 14(4):443-455. (doi:10.1007/s10456-011-9227-z).*
J. Larkin et al., "Combined Nivolumab and Ipilimumab or Monotherapy in Untreated Melanoma" N Engl JMed 2015; 373: p. 23-24.
Drug Interview Form of OPDIVO(R) Intravenous Infusion 20mg• 100 mg, revised in Apr. 2016 (version 9), with partial English translation thereof.
Properties and Handling of Adverse Events of an Anti-CTLA-4 Antibody, Ipilimumab (YERVOY(R)), dated Aug. 2, 2015, issued by the Committee on Safety of New Drugs for Malignant Melanoma of the Japanese Dermatological Association, with English partial translation thereof.
Shigehisa Kitano, "Gan Men'ek Ryoho no Breakthrough, Clinical development of immune check point inhibitors", Journal of Clinical and Experimental Medicine, Feb. 13, 2016, vol. 256, No. 7, pp. 793-797, with English partial translation thereof.
International Search Report dated Sep. 26, 2017 in International Application No. PCT/JP2017/024244.
International Preliminary Report on Patentability dated Jan. 10, 2019 in International Application No. PCT/JP2017/024244.

* cited by examiner

*Primary Examiner* — Robert S Landsman
(74) *Attorney, Agent, or Firm* — Wenderoth, Lind & Ponack, L.L.P.

(57) ABSTRACT

The present invention provides a novel method of obtaining data for predicting the onset of an adverse event due to administration of at least one antibody drug selected from an anti-PD-1 antibody, an anti-PD-L1 antibody, an anti-CTLA4 antibody, and an antigen-binding fragment thereof, or a novel method of predicting the onset of the adverse event. More specifically, the present invention provides a method of obtaining data for predicting the onset of an adverse event or a method of predicting the onset of the adverse event, comprising measuring a level of at least one marker selected from sCD163 and CXCL5 in a biological sample collected from a subject administered the antibody drug.

10 Claims, 3 Drawing Sheets

METHOD OF ALTERING AN ANTIBODY-RELATED ADVERSE EVENT BASED ON SCD163 AND/OR CXCL5 LEVELS

CROSS-REFERENCE TO RELATED APPLICATIONS

This application is based upon and claims the benefit of priority from Japanese Patent Application No. 2016-131913, filed on Jul. 1, 2016; the entire contents of which are incorporated herein by reference.

TECHNICAL FIELD

The present invention relates to a novel method of predicting the onset of an adverse event due to administration of at least one antibody drug selected from an anti-PD-1 antibody, an anti-PD-L1 antibody, an anti-CTLA4 antibody, and an antigen-binding fragment thereof.

BACKGROUND ART

Cancer cells prevent attacks of immune cells by decreasing the activity of the immune cells that attack the cancer cells. This mechanism is referred to as "immune checkpoint", Therefore, inhibition of this "immune checkpoint" can activate the action of immune cells again to attack cancer cells. An immune checkpoint inhibitor is a drug that activates immune cells whose activity was decreased by cancer cells to attack the cancer cells.

Specific examples of the immune checkpoint inhibitor include an anti-PD-1 antibody and an anti-CTLA4 antibody. Nivolumab and pembrolizumab, which are anti-PD-1 antibodies, have been known to be useful for treatment of malignant melanoma, and have also been reported to have therapeutic effects on non-small-cell lung cancer and renal cell carcinoma (Patent Document 1, Non-Patent Document 1). Ipilimumab or tremelimumab, which is an anti-CTLA4 antibody, has also been known to be useful for treatment of melanoma and other malignant tumors (Patent Document 2).

Meanwhile, it has been known that autoimmune-related adverse events due to administration of an immune checkpoint inhibitor frequently occur compared with a conventional drug. For example, it has been reported that the incidence of adverse events of grade 3 or higher when an anti-PD-1 antibody (nivolumab) or an anti-CTLA4 antibody (ipilimumab) is administered to patients with radically unresectable malignant melanoma is 163% for nivolumab alone, 272% for ipilimumab alone, and 55.0% for combination of nivolumab and ipilimumab (Non-Patent Document 1).

As the adverse events due to administration of an immune checkpoint inhibitor, life-threatening serious adverse events such as pituitarism, autoimmune colitis, interstitial pneumonia, and severe hepatic disorder exist. Since the timing of appearance and the progression rate, etc., of these adverse events cannot be predicted, patients often are not aware of the onset at home and are in fatal conditions at consultation.

Therefore, development of a technical means that can predict the possibility (risk) of the onset before the onset of an adverse event due to administration of an immune checkpoint inhibitor has been required.

PRIOR ART REFERENCES

Non-Patent Document

Non-Patent Document 1: Larkin J, Chiarion-Sileni V, Gonzalez R, Grob J J, Cowey C L, Lao C D, et al. Combined Nivolumab and Ipilimumab or Monotherapy in Untreated Melanoma. N Engl J Med 2015; 373: p. 23-34.

Patent Documents

Patent Document 1: JP 2016-064989 A
Patent Document 2 JP 2015-526525

SUMMARY OF THE INVENTION

An object of the present invention is to provide a novel technical means that predicts the possibility (risk) of the onset of an adverse event in a subject administered at least one antibody drug selected from an anti-PD-1 antibody, an anti-PD-L1 antibody, and an anti-CTLA4 antibody, which are immune checkpoint inhibitors, and an antigen-binding fragment thereof.

The present inventors have found that the onset of an adverse event due to administration of the antibody drug can be predicted by measuring a level of at least one marker selected from sCD163 and CXCL5 in a biological sample collected from a subject administered at least one antibody drug selected from an anti-PD-1 antibody, an anti-PD-L1 antibody, an anti-CTLA4 antibody, and an antigen-binding fragment thereof.

According to the present invention, the following invention is provided.

(1) A method of obtaining data for predicting an onset of an adverse event due to administration of at least one antibody drug selected from an anti-PD-1 antibody, an anti-PD-L1 antibody, an anti-CTLA4 antibody, and an antigen-binding fragment thereof, the method comprising:
measuring a level of at least one marker selected from sCD163 and CXCL5 in a biological sample collected from a subject administered the above-mentioned antibody drug.
(2) The method according to (1), wherein the above-mentioned anti-PD-1 antibody is nivolumab.
(3) The method according to (1) or (2), wherein the above-mentioned anti-CTLA4 antibody is ipilimumab.
(4) The method according to any one of (1) to (3), wherein the above-mentioned antibody drug is an anticancer agent.
(5) The method according to any one of (1) to (4), wherein the above-mentioned adverse event is an immune-related adverse event.
(6) The method according to any one of (1) to (5), wherein the above-mentioned marker is a combination of sCD163 and CXCL5.
(7) The method according to any one of (1) to (6), comprising obtaining comparative data between a level of the marker in a biological sample collected from a subject administered the above-mentioned antibody drug and a level of a corresponding marker in a biological sample collected from a subject before administration of the above-mentioned antibody drug.
(8) The method according to (7), wherein the level of the above-mentioned marker in a biological sample collected from a subject administered the above-mentioned antibody drug or the above-mentioned comparative data serves as an index of an onset of an adverse event.
(9) The method according to (7), wherein the level of the above-mentioned marker in a biological sample collected from a subject administered the above-mentioned antibody drug or the above-mentioned comparative data serves as an index of administration of a steroid to a subject.
(10) The method according to claim 8 or 9, wherein the comparative data serves as an index of an onset of an adverse event.

(11) A method of predicting an onset of an adverse event due to administration of at least one antibody drug selected from an anti-PD-1 antibody, an anti-PD-L1 antibody, an anti-CTLA4 antibody, and an antigen-binding fragment thereof, the method comprising:
measuring a level of at least one marker selected from sCD163 and CXCL5 in a biological sample collected from a subject administered the above-mentioned antibody drug.
(12) The method according to (11), comprising comparing level of the marker in a biological sample collected from a subject administered the above-mentioned antibody drug with a level of a corresponding marker in a biological sample collected from a subject before administration of the above-mentioned antibody drug.
(13) The method according to (12), which predicts that a possibility of an onset of an adverse event is high when the level of the marker in a biological sample collected from a subject administered the above-mentioned antibody drug is out of a predetermined threshold.
(14) A method of monitoring an adverse event due to administration of at least one antibody drug selected from an anti-PD-1 antibody, an anti-PD-L1 antibody, an anti-CTLA4 antibody, and an antigen-binding fragment thereof, the method comprising:
measuring a level of at least one marker selected from sCD163 and CXCL5 in a biological sample collected from a subject administered the above-mentioned antibody drug.
(15) A marker comprising sCD163 or CXCL5 for, in a subject administered at least one antibody drug selected from an anti-PD-1 antibody, an anti-PD-L1 antibody, an anti-CTLA4 antibody, and an antigen-binding fragment thereof, predicting an onset of an adverse event due to administration of the antibody drug.
(16) A diagnostic agent comprising at least one component selected from an anti-sCD163 antibody, an anti-CXCL5 antibody, and an antigen-binding fragment thereof, for predicting an onset of an adverse event due to administration of at least one antibody drug selected from an anti-PD-1 antibody, an anti-PD-L1 antibody, an anti-CTLA4 antibody, and an antigen-binding fragment thereof.
(17) A diagnostic kit comprising at least one component selected from an anti-sCD163 antibody, an anti-CXCL5 antibody, and an antigen-binding fragment thereof for predicting an onset of an adverse event due to administration of at least one antibody drug selected from an anti-PD-1 antibody, an anti-PD-L1 antibody, an anti-CTLA4 antibody, and an antigen-binding fragment thereof.

According to the present invention, measuring a level of at least one marker selected from sCD163 and CXCL5 in a biological sample collected from a subject administered at least one antibody drug selected from an anti-PD-1 antibody, an anti-PD-L1 antibody, an anti-CTLA4 antibody, and an antigen-binding fragment thereof can predict the onset of an adverse event due to administration of the above-mentioned antibody drug. The method of the present invention is advantageous in prevention, suppression, or delay of the onset of an adverse event or relief of an adverse event by administration of a drug after predicting the onset of an adverse event in advance. Use of the method of the present invention can predict the onset of an adverse event and reduce disturbance by an adverse event. Use of the present invention can predict the onset of an adverse event due to administration of the above-mentioned antibody drug by a simple means.

BRIEF DESCRIPTION OF THE DRAWINGS

FIG. 1A is a graph showing change in serum sCD163 concentration before and after administration of nivolumab in each patient administered nivolumab. FIG. 1B is a graph showing change in serum CXCL5 concentration before and after administration of nivolumab in each patient administered nivolumab.

FIG. 2 is an ROC curve prepared based on the fluctuation ratio data on sCD163 concentration

DETAILED DESCRIPTION OF THE INVENTION

Figure 1A:
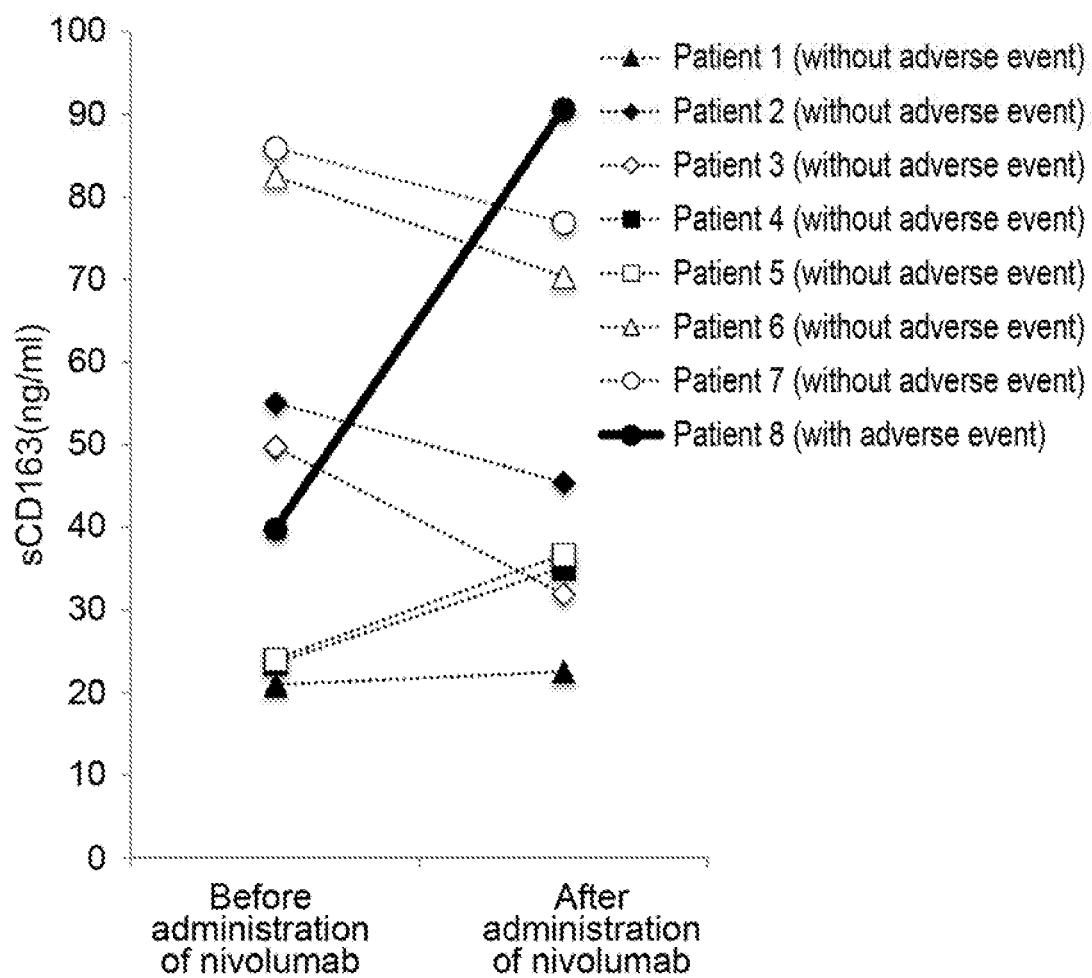
FIGS. 1A-1B.

Method of Obtaining Data/Method of Predicting Onset of Adverse Event

One of the characteristics of the method of the present invention is measuring a level of at least one marker selected from sCD153 and CXCL5 in a biological sample collected from a subject administered at least one antibody drug selected from an anti-PD-1 antibody, an anti-PD-L1 antibody, an anti-CTLA4 antibody, and an antigen-binding fragment thereof. Here, the marker to be used is preferably a combination of sCD163 and CXCL5. According to the method, the onset of an adverse event can be predicted based on the obtained data.

The method of the present invention includes obtaining comparative data between a level of the above-mentioned marker in a biological sample collected from a subject administered the above-mentioned antibody drug and a level of a corresponding marker hi a biological sample collected from the subject before administration of the antibody drug. As used herein, comparative data mean, for example, a difference in or a ratio of the above-mentioned level. The level of the above-mentioned marker in a biological sample collected from a subject administered the above-mentioned antibody drug or the above-mentioned comparative data serves as an index of the onset of an adverse event. Furthermore, the level of the above-mentioned marker in a biological sample collected from a subject administered the above-mentioned antibody drug or the above-mentioned comparative data serves as an index of administration of a drug, preferably a steroid, to a subject. As the index of the onset of the above-mentioned adverse event or the index of administration of a drug, preferably a steroid, to a subject, the above-mentioned comparative data are preferable. The level of the marker will be mentioned later.

sCD163, CXCL5

The marker of the present invention for, in a subject administered at least one antibody drug selected from an anti-PD-1 antibody, an anti-PD-L1 antibody, an anti-CTLA4 antibody, and an antigen-binding fragment thereof, predicting the onset of an adverse event due to administration of the antibody drug comprises sCD163 or CXCL5.

"CD163" in the present invention is a single-chain transmembrane protein, a member of the scavenger receptor cysteine-rich family, and is interchangeably used with "M130". "sCD163 (soluble CD163)" is CD163 that became soluble after cleaved. "sCD163" In the present invention may include an altered form, an isoform, and a species homolog of sCD163.

"CXCL5" in the present invention is a neutrophil/monocyte chemotactic protein, a member of the ELR$^+$ group having an ELR motif on the N-terminal side of a CXC motif, is interchangeably used with "LIX" and "GCP-2", and may include an altered form, an isoform, and a species homolog of CXCL5.

The level of at least one marker selected from sCD163 and CXCL5 in a biological sample is, for example, the concentration or amount of the above-mentioned marker in a biological sample, and preferably the concentration of sCD163 or the concentration of CXCL5 in a biological sample. Examples of the concentration of sCD163 to be measured include the concentration in the range of 1 ng/mL to 500 ng/mL. Examples of the concentration of CXCL5 to be measured include the concentration in the range of 10 pg/mL to 10,000 pg/mL, 10 pg/mL to 5,000 pg/mL.

Anti-PD-1 Antibody, Anti-PD-L1 Antibody, Anti-CTLA4 Antibody

"Antibody" in the present invention is a full-length antibody and includes a glycoprotein comprising at least two heavy chains (H) and two light chains (L) that are joined by a disulfide bond. Each heavy chain is composed of a heavy-chain variable region (hereinafter sometimes abbreviated to as $V_H$) and a heavy-chain constant region. The heavy-chain constant region is composed of three domains of $C_H1$, $C_H2$, and $C_H3$. Each light chain is composed of a light-chain variable region (hereinafter sometimes abbreviated as $V_L$) and a light-chain constant region. The light-chain constant region is composed of one domain of $C_L$. The $V_H$ and $V_L$ regions are further subdivided into highly variable regions called complementarity-determining regions (CDRs), and in these regions, highly conservative regions called framework regions (FRs) are scattered. The above-mentioned heavy-chain and light-chain variable regions include a binding domain that interacts with antigens.

Examples of the "antibody" include a monoclonal antibody, a polyclonal antibody, a bispecific antibody, a low-molecular-weight antibody, a domain antibody, a synthetic antibody, a chimeric antibody, a humanized antibody, a human antibody, an antibody conjugate, a single-chain antibody, an antibody derivative, an antibody analog, and an antigen-binding fragment of each of them.

"Antigen-binding fragment" of the antibody in the present invention (or also simply referred to as "antibody fragment") represents one or more fragments of an antibody having ability to specifically bind to an antigen (for example, PD-1). Examples of the binding fragment included in the "antigen-binding fragment" of the antibody include (I) a Fab fragment which is a univalent fragment composed of $V_1$, $V_H$, $C_L$, and $C_H1$ domains, (ii) an $F(ab')_2$ fragment which is a bivalent fragment comprising two Fab fragments bonded by a disulfide bridge in a hinge region, (iii) an Fd fragment composed of $V_H$ and $C_H1$ domains, (iv) an Fv fragment composed of $V_L$ and $V_H$ domains of a single arm of the antibody, (v) a dAb fragment composed of a $V_H$ domain, or (vi) an isolated complementarity-determining region (CDR). Furthermore, $V_L$ and $V_H$, which are two domains of an Fv fragment, are encoded by different genes, and can be joined by a synthetic linker that can produce them as a single protein chain using a recombinant technique, and in this chain, a pair of the $V_L$ and $V_H$ regions can form a univalent molecule (single chain Fv (scFv)). Such a single chain antibody is also included in the "antigen-binding fragment" of the antibody.

"PD-1" in the present invention is an immunoreceptor that mediates a signal for immune response regulation, and a type I membrane protein belonging to the CD28/CTLA-4 family. "PD-1" in the present invention is interchangeably used with "programmed death 1", "programmed cell death 1", "protein PD-1", "PD1", "PDCD1", and "hPD-1", and may include an altered form, an isoform, and a species homolog of PD-1, and an analog having at least one epitope common to PD-1.

"Anti-PD-1 antibody" In the present invention is not particularly limited as long as the effect of the present invention is not impaired, and may be an antibody that specifically binds to PD-1. The antibody may be an antibody that specifically recognizes part of the structure of an amino acid sequence, or may be an antibody that specifically recognizes the overall structure. The above-mentioned antibody is not particularly limited, and examples thereof include nivolumab, pembrolizumab, or lambrolizumab, and nivolumab or pembrolizumab is preferable.

"CTLA4" in the present invention is a regulator that suppresses the activation of T cells, is interchangeably used with "cytotoxic T-lymphocyte-associated antigen-4", "CTLA-4", "CTLA-4 antigen", and "CD152", and may include an altered form, an isoform, and a species homolog of human CTLA4, and an analog having at least one epitope common to CTLA4.

"Anti-CTLA4 antibody" in the present invention is not particularly limited as long as the effect of the present invention is not impaired, and may be an antibody that specifically binds to CTLA4. The antibody may be an antibody that specifically recognizes part of the structure of an amino acid sequence, or may be an antibody that specifically recognizes the overall structure. The above-mentioned antibody is not particularly limited, and is preferably ipilimumab or tremelimumab.

"PD-L1" in the present invention is a ligand for PD-1, is interchangeably used with "CD274", "programmed cell death 1 ligand 1", "PDCD1L1", "B7-H", and "B7H1", and may include an altered form, an isoform, and a species homolog of PD-L1, and an analog having at least one epitope common to PD-L1.

"Anti-PD-L1 antibody" in the present invention is not particularly limited as long as the effect of the present invention is not impaired, and may be an antibody that specifically binds to PD-L1. The antibody may be an antibody that specifically recognizes part of the structure of an amino acid sequence, or may be an antibody that specifically recognizes the overall structure. The above-mentioned antibody is not particularly limited, and is preferably MPDL3280A (RG7446) or atezolizumab.

"Antibody drug" In the present invention is at least one selected from an anti-PD-1 antibody, an anti-PD-L1 antibody, an anti-CTLA4 antibody, and an antigen-binding fragment thereof. Only one antibody mentioned above or antigen-binding fragment thereof may be administered to a subject, or a combination of two or more antibodies mentioned above or antigen-binding fragments thereof may be simultaneously or separately administered to a subject. Examples of the combination of two or more antibodies mentioned above or antigen-binding fragments thereof include a combination of an anti-PD-1 antibody and an anti-CTLA4 antibody. The method of administering the above-mentioned antibody is not particularly limited, and intravenous administration is preferable.

The subject of the present invention is preferably a human, and more preferably a human suffering from a disease that can be treated by administration of at least one antibody drug selected from an anti-PD-1 antibody, an anti-PD-L1 antibody, an anti-CTLA4 antibody, and an antigen-binding fragment thereof, or a human having a possibility to suffer from the disease. As used herein, "treatment" includes not only treatment of an established pathological condition but also prevention of a pathological condition that may be established in the future.

The disease that can be treated by administration of at least one antibody drug selected from an anti-PD-1 antibody, an anti-PD-L1 antibody, an anti-CTLA4 antibody, and an antigen-binding fragment thereof is not particularly limited, and examples thereof include cancer, sarcoma, or malignant mesothelioma. Therefore, the above-mentioned antibody drug may be an anticancer agent. Specific examples of cancer, sarcoma, or malignant mesothelioma include skin cancer such as malignant melanoma (melanoma) (e.g., metastatic malignant malignant melanoma, radically unresectable malignant melanoma), squamous cell carcinoma of skin, extramammary Paget's disease, or Merkel cell carcinoma; renal cancer (e.g., renal cell carcinoma, clear cell carcinoma); prostate cancer (e.g., hormone-refractory prostate adenocarcinoma); breast cancer; colon cancer; lung cancer (e.g., non-small-cell lung cancer); bone cancer; pancreatic cancer; head and neck cancer; cutaneous or intraorbital malignant melanoma; uterine cancer; ovarian cancer; rectal cancer; anal cancer; gastric cancer; testicular cancer; uterine cancer; fallopian tube carcinoma; endometrial carcinoma; cervical carcinoma; vaginal carcinoma; vulvar carcinoma; esophageal cancer; small intestinal cancer; colorectal cancer; endocrine cancer; thyroid cancer; parathyroid cancer; adrenal cancer; soft tissue sarcoma; multiple myeloma; urethral cancer; penile cancer; chronic or acute leukemia (e.g., acute myeloid leukemia, chronic myeloid leukemia, acute lymphoblastic leukemia, chronic lymphocytic leukemia); childhood solid cancer; advanced solid cancer; bladder cancer; kidney or ureter cancer; renal pelvic carcinoma; urothelial cancer; central nervous system (CNS) tumor; lymphoma (e.g., lymphocytic lymphoma, primary CNS lymphoma, non-Hodgkin's lymphoma, Hodgkin's lymphoma (Hodgkin's disease), T cell lymphoma); malignant pleural mesothelioma; malignant pericardial mesothelioma; malignant peritoneal mesothelioma; tumor angiogenesis; spinal tumor; brainstem glioma; pituitary adenoma; Kaposi's sarcoma; squamous cell carcinoma; planocellular carcinoma; environmentally induced cancer comprising asbestos-induced cancer; or a combination thereof, and skin cancer is preferable, and malignant melanoma, squamous cell carcinoma of skin, extramammary Paget's disease, or Merkel cell carcinoma is more preferable.

The adverse event due to administration of the antibody drug in the present invention is not particularly limited, and is preferably an immune-related adverse event (adverse event that is presumed to be immune-related: IrAE) (see, for example, Drug Interview Form of OPDIVO® Intravenous Infusion 20 mg-100 mg, revised in April 2016 (version 9); Properties and Handling of Adverse Events of an Anti-CTLA-4 Antibody, Ipilimumab (YERVOY®), dated Aug. 24, 2015, issued by the Committee on Safety of New Drugs for Malignant Melanoma of the Japanese Dermatological Association). Specific embodiments of the above-mentioned adverse event of the present invention include interstitial lung disease, myasthenia gravis, myositis, colitis, type 1 diabetes mellitus, hepatic dysfunction (hepatic disorder), pulmonary disorder such as hepatitis (e.g., autoimmune pneumonia), pituitarism such as hypopituitarism or hypophysitis, thyroid dysfunction such as hypothyroidism, neuropathy, nephropathy, encephalitis, adrenal disorder such as adrenal insufficiency, severe skin disorder, venous thromboembolism, infusion reaction, psoriasis, psoriasiform rash, diarrhea (e.g., severe diarrhea), rheumatoid arthritis, uveitis, episcleritis, bursitis, exacerbation of radiodermatitis, chronic inflammatory demyelinating polyneuropathy (hereinafter also referred to as demyelinating polyneuropathy), biliary tract disorder, or nephritis, and pituitarism is preferable.

The immune-related adverse event (IrAE) has been known to occur, for example, after 8 weeks or 8 to 12 weeks after administration.

The immune-related adverse event is evaluated by "grade" or "IrAE evaluation". Here, "irAE evaluation" is an index representing the seriousness of a disease, and is represented by 1 to 3. In the irAE evaluation, 1 represents a condition that "does not require additional therapeutic intervention due to irAE", 2 represents a condition that "requires drug intervention, etc., due to irAE, but does not require hospitalization treatment or does not require interruption of treatment", and 3 represents a condition that "requires drug intervention, etc., accompanied by hospitalization due to irAE and requires interruption of treatment". The correspondence between "irAE evaluation" and "grade" varies depending on each disease.

Measurement Method

As the biological sample that can be used in the present invention, serum, plasma, blood, or urine or the like is exemplified, and serum is preferable.

As the timing of collection of the above-mentioned biological sample, before onset of the above-mentioned adverse event is exemplified from the viewpoint of prevention of the onset of the adverse event. Examples of before onset of the above-mentioned adverse event include before administration of the above-mentioned antibody drug and after administration of the above-mentioned antibody drug or both. Here, before administration of the above-mentioned antibody drug may also include at the time of or immediately after administration of the above-mentioned antibody drug in addition to before administration of the above-mentioned antibody drug. Furthermore, examples of after administration of the above-mentioned antibody drug include within 12 weeks, preferably within 8 weeks, and more preferably 6 weeks after administration of the above-mentioned antibody drug. Before administration and after administration of the above-mentioned antibody drug may be before the first administration and after the first administration of the above-mentioned antibody drug, respectively.

Furthermore, with respect to the timing of collection of the above-mentioned biological sample, from the viewpoint of monitoring and confirmation of the effect of a drug mentioned later, the period after administration of the above-mentioned antibody drug as after administration of the above-mentioned antibody drug is not limited, and furthermore, measurement may be performed twice or more after administration.

For measurement of sCD163 or CXCL5, any currently known method can be adopted. Examples thereof include immunoassay, electrophoresis, Western blotting, and mass spectrometry, and immunoassay is preferable.

Examples of the immunoassay include immunonephelometry and enzyme immunoassay. The immunoassay is an immunoassay in which measurement is performed using proteins, etc., as antigens. The antibody is not particularly limited as long as the effect of the present invention is not impaired, and at least one component selected from an anti-sCD163 antibody, an anti-CXCL5 antibody, and an antigen-binding fragment thereof can be used, and preferably a polyclonal antibody or a monoclonal antibody thereof can be used. As at least one component selected from an anti-sCD163 antibody, an anti-CXCL5 antibody, and an antigen-binding fragment thereof, a commercially available antibody can be used, or the component can also be produced by a well-known method. The anti-sCD163 antibody or anti-CXCL5 antibody is not particularly limited as long as it can specifically bind to sCD163 or CXCL5, respectively, and it may be an antibody that specifically recognizes part of the structure of an amino acid sequence, or may be an antibody that specifically recognizes the overall structure.

The immunonephelometry is not particularly limited as long as it is a method in which sCD163 or CXCL5 in a biological sample is reacted with at least one component selected from an anti-sCD163 antibody, an anti-CXCL5 antibody, and an antigen-binding fragment thereof to cause an antigen-antibody reaction and from the degree of the resultant turbidity, the level of sCD163 or CXCL5 is measured. Examples of such method include TIA, latex immunonephelometry, and nephelometry. The TIA is a method in which the degree of turbidity is measured at a specific absorbance in immunonephelometry. The latex immunonephelometry is a method in which measurement is performed using at least one component selected from an anti-sCD163 antibody, an anti-CXCL5 antibody, and an antigen-binding fragment thereof as an antibody bound to a latex particle in immunonephelometry. Furthermore, the nephelometry is a method in which the degree of turbidity is measured as scattered light by gathering light scattered to a certain angle or more in immunonephelometry.

As the enzyme immunoassay, EIA, such as ELISA, using a plate as a support medium can be exemplified. First, at least one component selected from an anti-sCD163 antibody, an anti-CXCL5 antibody, and an antigen-binding fragment thereof is directly or indirectly bound as a primary antibody to a solid phase.

When sCD163 or CXCL5 is measured by the enzyme immunoassay, for example, reaction is performed by adding a biological sample for measurement of sCD163 or CXCL5 to the primary antibody bound to the solid phase. After reaction for a certain period of time, the solid phase is washed, and a secondary labeled antibody is added to perform a second reaction. The solid phase is washed again, and a labeled moiety bound to the solid phase is measured.

In the immunoassay using the secondary labeled antibody mentioned above, an enzyme such as horseradish peroxidase (HRP) alkaline phosphatase can be used as a labeling substance. For example, when HRP-labeled antibody is utilized, known DAB, TMB, OPD or the like can be used as a substrate. Examples of the labeling substance include not only enzymes such as HRP, but also any labelable substances comprising labeling metals such as a gold colloid and europium, various chemical or biological fluorescent substances such as FITC, rhodamine, Texas Red, Alexa, and GFP, and radioactive materials such as $^{32}P$ and $^{51}Cr$, and the like. When a labeling substance is used in the present invention, an avidin-biotin system or a streptavidin-biotin system can also be used. In that case, for example, streptavidin or avidin that is labeled by an enzyme such as HRP can be used together with a biotin-labeled secondary labeled antibody. Chemiluminescent immunoassay using a luciferase-labeled antibody, fluorescent immunoassay using a fluorochrome-labeled antibody, flow cytometry, and the like can be exemplified.

As the electrophoresis, generally SDS-PAGE can be exemplified. In addition, a method using cellulose acetate as a support medium and the like can be exemplified. As staining of proteins, Coomassie Brilliant Blue, Ponceau S staining, amido black staining, a method utilizing direct enzyme activity, and the like are exemplified.

Detection by Western blotting is also effective. In other words, an electrophoresed gel is transcribed to a nitrocellulose membrane or PVDF membrane or the like. Next, at least one component selected from an anti-sCD163 antibody, an anti-CXCL5 antibody and an antigen-binding fragment thereof, which are primary antibodies, and further HRP-labeled anti-IgG, etc., which is a secondary labeled antibody, are reacted. Next, a color is developed using an HRP coloring reagent, and sCD163 or CXCL5 can be measured according to the degree of coloring of a band corresponding to sCD163 or CXCL5.

Examples of the mass spectrometry include an analytical method using a mass spectrometer. For example, methods using surface enhanced laser desorption/Ionization time-of-flight mass spectrometry (SELDI-TOF MS), matrix-assisted laser desorption/ionization time-of-flight mass spectrometry (MALDI-TOF MS), and electrospray ionization (ESI) can be exemplified. SELDI-TOF MS is preferable because a reproducible ion spectrum with a high S/N ratio can be obtained since impurities are removed while uniformly capturing a target substance in a functional group on the surface of a tip and ionization is performed by a laser beam.

Prediction of Onset of Adverse Event

In the present invention, it is possible to predict the onset of an adverse event due to administration of the above-mentioned antibody drug using data obtained by measurement as mentioned above. In the above-mentioned prediction step, it is preferable to compare a level of at least one marker selected from sCD163 and CXCL5 in a biological sample collected from a subject administered (namely, after administration of) at least one antibody drug selected from an anti-PD-1 antibody, an anti-PD-L1 antibody, an anti-CTLA4 antibody, and an antigen-binding fragment thereof with a level of a corresponding marker in a biological sample collected from a subject before administration.

Therefore, according to another embodiment of the present invention, a step of measuring a level of at least one marker selected from sCD163 and CXCL5 in a biological sample collected from a subject before administration of at least one antibody drug selected from an anti-PD-1 antibody, an anti-PD-L1 antibody, an anti-CTLA4 antibody, and an antigen-binding fragment thereof may be included. When the level of the above-mentioned marker was measured twice or more after administration of the above-mentioned antibody drug, levels of the above-mentioned marker at two optional measurement points may be compared.

A level of at least one marker selected from sCD163 and CXCL5 in a biological sample can be measured by the above-mentioned measurement method, and measurement by ELISA is preferable.

Furthermore, according to a preferred embodiment of the present invention, the above-mentioned prediction step does not include judgment by a physician.

Furthermore, according to another embodiment of the present invention, prediction of the onset of an adverse event includes prediction that an adverse event has occurred when the grade of the adverse event is low, in addition to prediction of the onset before an adverse event occurs. Here, the low grade of an adverse event means preferably 1 to 2. According to another embodiment of the present invention, prediction of the onset of an adverse event also includes prediction that an adverse event has occurred when an immune-related adverse event (irAE) evaluation is low. Here, the low IrAE evaluation means preferably 1 to 2.

In prediction of the onset of an adverse event, statistical processing may be performed by comparing a difference or ratio of a level of at least one marker selected from sCD163 and CXCL5 in a biological sample before and after administration of the above-mentioned antibody drug in a subject (group) with an adverse event with a difference or ratio of a corresponding marker in a subject (group) without an adverse event. When a level of the above-mentioned marker is measured twice or more after administration of the above-mentioned antibody drug, a difference or ratio of levels of the above-mentioned marker at two optional measurement points may be compared. As a result, when there is a significant difference between a subject (group) with an adverse event and a subject (group) without an adverse event, the difference or ratio of the level of the marker used can be used as an index for predicting the possibility of the onset of an adverse event. As the above-mentioned statistical processing, U test (nonparametrical) or paired t-test (in the case of normal distribution) is exemplified.

Prediction of the onset of an adverse event due to administration of the above-mentioned antibody drug of the present invention can be performed based on, for example, an index of a high possibility of the onset of an adverse event when a level of sCD163 in a biological sample collected from a subject after administration of the above-mentioned antibody drug is higher than a level of sCD163 in a biological sample of a subject before administration.

When a level of sCD163 in a biological sample collected from a subject after administration of the above-mentioned antibody drug is preferably 1.2-fold or more, more preferably 1.5-fold or more, still more preferably 1.6-fold or more, yet more preferably 1.8-fold or more, and yet still more preferably 2-fold or more higher than a level of sCD163 in a biological sample collected from a subject before administration, it is possible to predict that the possibility of the onset of an adverse event is high. When a concentration of sCD163 in a biological sample collected from a subject after administration of the above-mentioned antibody drug is higher by preferably 10 ng/mL, more preferably 15 ng/mL, still more preferably 20 ng/mL, and yet more preferably 40 ng/mL or more than a concentration of sCD163 in a biological sample of a subject before administration, it is possible to predict that the possibility of the onset of an adverse event is high.

Prediction of the onset of an adverse event due to administration of the above-mentioned antibody drug of the present invention can be performed based on, for example, an index of a high possibility of the onset of an adverse event when a level of CXCL5 in a biological sample collected from a subject after administration of the above-mentioned antibody drug is higher than a level of CXCL5 In a biological sample of a subject before administration.

When a level of CXCL5 in a biological sample collected from a subject after administration of the above-mentioned antibody drug is preferably 1.05-fold or more, more preferably 1.1-fold or more, still more preferably 1.2-fold or more, and yet more preferably 1.3-fold or more higher than a level of CXCL5 in a biological sample of a subject before administration, it is possible to predict that the possibility of the onset of an adverse event is high. When a concentration of CXCL5 in a biological sample collected from a subject after administration of the above-mentioned antibody drug is higher by preferably 50 pg/mL, more preferably 100 pg/mL, and still more preferably 150 pg/mL or more than a concentration of CXCL5 In a biological sample of a subject before administration, it is possible to predict that the possibility of the onset of an adverse event is high.

According to one embodiment of the present invention, when a level of at least one marker selected from sCD163 and CXCL5 measured in a subject is out of a predetermined threshold for the onset of an adverse event due to administration of the above-mentioned antibody drug, it is possible to predict that the possibility of the onset of an adverse event is high. "Out of a predetermined threshold" means, for example, "when the level of the above-mentioned marker is the same as a predetermined threshold or higher than the threshold", and when a threshold has an upper limit and a lower limit as mentioned later, it means "when the level of the above-mentioned marker is the same as the upper limit or higher than the upper limit, or the same as the lower limit or lower than the lower limit".

According to another embodiment mentioned above, it is possible to set a threshold in advance based on a level difference or level ratio of at least one marker selected from sCD163 and CXCL5 before and after administration of the above-mentioned antibody drug in a subject (group) with an adverse event or a subject (group) without an adverse event. When the level of the above-mentioned marker is measured twice or more after administration of the above-mentioned antibody drug, it is possible to set a threshold in advance based on a difference or ratio of levels of the above-mentioned marker at two optional measurement points. Prediction of the onset of an adverse event may be performed by comparing the above-mentioned threshold with a level difference or level ratio of a corresponding marker in a subject in whom the onset of an adverse event is predicted.

Any person skilled in the art can appropriately set a threshold based on a level difference or level ratio of a marker selected from sCD163 and CXCL5 before and after administration of the above-mentioned antibody drug in a subject (group) with an adverse event, a subject (group) without an adverse event, or a subject (group) with an adverse event and a subject (group) without an adverse event (hereinafter also referred to as all subjects (group)). The threshold is not particularly limited, and for example, a mean, a median, and an X percentile of a level difference or ratio of the above-mentioned marker in a subject (group) with an adverse event, a subject (group) without an adverse event, or all subjects (group) can be used, and a mean is preferable. Here, as X, an optional numerical value can be selected, and 3, 5, 10, 15, 20, 30, 40, 60, 70, 80, 85, 90, 95, or 97 can be appropriately used. The threshold may be one, or plural thresholds may be set according to the type of an adverse event, the type of an antibody drug to be administered, the condition of a subject to whom an antibody drug is administered, the type of a marker to be measured or the like or a combination thereof.

As the threshold, for example, it is possible to set a specific numerical value range based on a mean, a median, an X percentile of a level difference or ratio of the above-mentioned marker in a biological sample collected from a subject (group) with an adverse event, a subject (group) without an adverse event, or all subjects (group). As the main numerical value, a mean is preferably used. The above-mentioned numerical value range can be determined based on a level difference or ratio of the above-mentioned marker before and after administration of the above-mentioned antibody drug in a subject (group) with an adverse event and a level difference or ratio of the above-mentioned marker before and after administration of the above-mentioned antibody drug in a subject (group) without an adverse event. Alternatively, the above-mentioned numerical value range can be determined based on a level difference or ratio of the above-mentioned marker before and after administration of the above-mentioned antibody drug in all subjects (group). As the above-mentioned numerical value range, for example, a standard deviation and a standard error of a level difference or ratio of the above-mentioned marker before and after administration of the above-mentioned antibody drug in all subjects (group) can be used. An upper limit and a lower limit may be set by preparing an ROC curve using a level difference or ratio of the above-mentioned marker before and after administration of the above-mentioned antibody drug in all subjects (group). Since the above-mentioned threshold has a numerical value range, an upper limit and a lower limit exist.

As the threshold, a specific upper limit and a specific lower limit can be set based on a level difference or ratio of the above-mentioned marker before and after administration of the above-mentioned antibody drug in a subject (group) with an adverse event and a level difference or ratio of the above-mentioned marker before and after administration of the above-mentioned antibody drug in a subject (group) without an adverse event, or based on a level difference or ratio of the above-mentioned marker before and after administration of the above-mentioned antibody drug in all subjects (group). Here, the upper limit and the lower limit each may independently be set, or may be set so that absolute values of the upper limit and the lower limit are the same. For example, the upper limit and the lower limit may be set by preparing an ROC curve using all subjects (group), or two optional X percentiles (X values are different each other) in all subjects (group) may be set as the upper limit and the lower limit.

With respect to the above-mentioned threshold, for example, when a ratio of a level of CXCL5 after administration of the above-mentioned antibody drug to a level of CXCL5 before administration of the antibody drug is preferably 1.05-fold or more, more preferably 1.1-fold or more, still more preferably 1.3-fold or more, and yet more preferably 1.5-fold or more, the ratio is considered significant, and the ratio can be used as the threshold. For example, when a ratio of a level of sCD163 after administration of the above-mentioned antibody drug to a corresponding level of sCD163 before administration of the antibody drug is preferably 1.3-fold or more, more preferably 1.5-fold or more, still more preferably 1.6-fold or more, yet more preferably 1.8-fold or more, and yet still more preferably 2-fold or more, the ratio is considered significant, and the ratio can be used as the threshold.

Furthermore, when the threshold is a value with a specific numerical value range based on a mean in all subjects (group) of a ratio of a level of CXCL5 after administration of the above-mentioned antibody drug to a level of CXCL5 before administration of the antibody drug, the numerical value range is, for example, 20 to 75%, preferably 30 to 60%, and particularly preferably 40 to 50%. When the threshold is a value with a specific numerical value range based on a mean in all subjects (group) of a difference between a level of CXCL5 after administration of the above-mentioned antibody drug and a level of CXCL5 before administration of the antibody drug, the numerical value range is, for example, 50 to 400 pg/mL, preferably 70 to 200 pg/mL, and particularly preferably 100 to 150 pg/mL. When the threshold is a value with a specific numerical value range based on a mean in all subjects (group) of a ratio of a level of sCD163 after administration of the above-mentioned antibody drug to a level of sCD163 before administration of the antibody drug, the numerical value range is, for example, 15 to 50%, preferably 20 to 40%, and more preferably 25 to 35%. When the threshold is a value with a specific numerical value range based on a mean in all subjects (group) of a difference between a level of sCD163 after administration of the above-mentioned antibody drug and a level of sCD163 before administration of the antibody drug, the numerical value range is, for example, 1 to 25 ng/mL, preferably 2 to 10 ng/mL, and more preferably 2.5 to 5 ng/mL.

When a specific upper limit and a specific lower limit are set as thresholds in the case of using a ratio of a level of CXCL5 after administration of the above-mentioned antibody drug to a level of CXCL5 before administration of the antibody drug, the upper limit is, for example, 20 to 60% and preferably 30 to 50%, and the lower limit is, for example, −60 to −20% and preferably −50 to −30%. When a specific upper limit and a specific lower limit are set as thresholds in the case of using a difference between a level of CXCL5 after administration of the above-mentioned antibody drug and a level of CXCL5 before administration of the antibody drug, the upper limit is, for example, 50 to 300 pg/mL and preferably 100 to 200 pg/mL, and the lower limit is, for example, −300 to −50 pg/mL and preferably −200 to −100 pg/mL. When a specific upper limit and a specific lower limit are set as thresholds in the case of using a ratio of a level of sCD163 after administration of the above-mentioned antibody drug to a level of sCD163 before administration of the antibody drug, the upper limit is, for example, 20 to 60%, 30 to 50%, and preferably 35 to 45%, and the lower limit is, for example, −40 to 0%, −30 to −10%, and preferably −25 to −15%. When a specific upper limit and a specific lower limit are set as thresholds in the case of using a difference between a level of sCD163 after administration of the above-mentioned antibody drug and a level of sCD163 before administration of the antibody drug, the upper limit is, for example, 7.5 to 25 ng/mL and preferably 7.5 to 12.5 ng/mL, and the lower limit is, for example, −15 to 2.5 ng/mL and preferably −2.5 to 2.5 ng/mL.

Comparison of a predetermined threshold with a level difference or level ratio in a subject enables prediction, judgement, or determination of the possibility of the onset of an adverse event in a subject.

According to another embodiment mentioned above, it is possible to set a threshold in advance based on a level of at least one marker selected from sCD163 and CXCL5 after administration of the above-mentioned antibody drug in a subject (group) with an adverse event or a subject (group) without an adverse event. Prediction of the onset of an adverse event may be performed by comparing the above-mentioned threshold with a level of a corresponding marker in a subject in which the onset of an adverse event is predicted.

Any person skilled in the art can appropriately set a threshold based on a level of at least one marker selected from sCD163 and CXCL5 after administration of the above-mentioned antibody drug in a subject (group) with an adverse event or a subject (group) without an adverse event. The threshold is not particularly limited, and for example, a mean, a median, and an X percentile of a level of the above-mentioned marker in a subject (group) with an adverse event or a subject (group) without an adverse event can be used, and a mean is preferable. Here, as X, an optional numerical value can be selected, and 3, 5, 10, 15, 20, 30, 40, 60, 70, 80, 85, 90, 95, or 97 can be appropriately used. The threshold may be one, or plural thresholds may be set according to the type of an adverse event, the type of an antibody drug to be administered, the condition of a subject to whom an antibody drug is administered, the type of a marker to be measured or the like or a combination thereof.

As the threshold, for example, it is possible to set a specific numerical value range based on a mean, a median, and an X percentile of a level of the above-mentioned marker in a biological sample after administration of the above-mentioned antibody drug in a subject (group) with an adverse event or a subject (group) without an adverse event. As the main numerical value, a mean is preferably used. The above-mentioned numerical value range can be determined based on a level of the above-mentioned marker after administration of the above-mentioned antibody drug in a subject (group) with an adverse event and a level of the above-mentioned marker after administration of the above-mentioned antibody drug in a subject (group) without an adverse event. Since the above-mentioned threshold has a numerical value range, an upper limit and a lower limit exist.

As the threshold, a specific upper limit and a specific lower limit can be set based on a level of the above-mentioned marker after administration of the above-mentioned antibody drug in a subject (group) with an adverse event and a level of the above-mentioned marker before and after administration of the above-mentioned antibody drug in a subject (group) without an adverse event. Here, the upper limit and the lower limit each may independently be set, or may be set so that absolute values of the upper limit and the lower limit are the same.

Comparison of a predetermined threshold with a level in a subject enables prediction, judgement, or determination of the possibility of the onset of an adverse event in a subject.

According to another embodiment of the present invention, a method of monitoring an adverse event due to administration of at least one antibody drug selected from an anti-PD-1 antibody, an anti-PD-L1 antibody, an anti-CTLA4 antibody, and an antigen-binding fragment thereof, comprising measuring a level of at least one marker selected from sCD163 and CXCL5 in a biological sample collected from a subject administered the antibody drug, is provided. The method can be performed by the same method as the method of obtaining data and the method of predicting the onset of an adverse event. The monitoring is advantageous in confirmation of the onset status of an adverse event in a subject or the grade or irAE evaluation of an adverse event over time.

The present invention also provides a marker comprising sCD163 or CXCL5 for, in a subject administered at least one antibody drug selected from an anti-PD-1 antibody, an anti-PD-L1 antibody, an anti-CTLA4 antibody, and an antigen-binding fragment thereof, predicting the onset of an adverse event due to administration of the antibody drug. As the above-mentioned marker, sCD163 alone or CXCL5 alone may be used, a combination of sCD163 and CXCL5 may be used, or a combination with other markers may be used. An embodiment of the marker can be performed according to a description on the method of obtaining data or the method of predicting the onset of an adverse event.

The present invention also provides a diagnostic agent for detecting at least one marker selected from sCD163 and CXCL5 and measuring a level thereof for, in a subject administered at least one antibody drug selected from an anti-PD-1 antibody, an anti-PD-L1 antibody, an anti-CTLA4 antibody, and an antigen-binding fragment thereof, predicting the onset of an adverse event due to administration of the antibody drug. By using the above-mentioned diagnostic agent, for example, it is possible to perform various measurement methods described above. Examples of the above-mentioned measurement methods include immunoassay, electrophoresis, Western blotting, mass spectrometry, and the like, and immunoassay is preferable. Here, the immunoassay also includes immunochromatography.

Therefore, as the above-mentioned diagnostic agent, for example, at least one component selected from an anti-sCD163 antibody, an anti-CXCL5 antibody, and an antigen-binding fragment thereof can be included. As the at least one component selected from an anti-sCD163 antibody, an anti-CXCL5 antibody, and an antigen-binding fragment thereof, that same as the antibody in the above-mentioned immunoassay can be used.

An embodiment of the diagnostic agent can be performed according to a description on the method of obtaining data or the method of predicting the onset of an adverse event.

The present invention also provides a diagnostic kit for detecting at least one marker selected from sCD163 and CXCL5 or measuring a level thereof for, in a subject administered at least one antibody drug selected from an anti-PD-1 antibody, an anti-PD-L1 antibody, an anti-CTLA4 antibody, and an antigen-binding fragment thereof, predicting the onset of an adverse event due to the antibody drug. In this kit, various reagents can be included as constituents according to a measurement method in order to perform various measurement methods described above. Examples of the above-mentioned measurement methods include immunoassay, electrophoresis, Western blotting, mass spectrometry, and the like, and immunoassay is preferable. Here, the immunoassay also includes immunochromatography.

Therefore, as the above-mentioned diagnostic kit, for example, at least one component selected from an anti-sCD163 antibody, an anti-CXCL5 antibody, and an antigen-binding fragment thereof can be included. The above-mentioned kit can further include a well-known reagent such as a coloring reagent for a labeling substance according to a measurement method to be performed.

An embodiment of the above-mentioned diagnostic kit can be performed according to a description on the method of obtaining data, the method of predicting the onset of an adverse event, or the diagnostic agent.

According to another embodiment of the present invention, the above-mentioned diagnostic kit can also be used for judgement of prophylactic administration of a drug or confirmation of the effect of a drug administered as mentioned later. According to another preferred embodiment of the present invention, the above-mentioned diagnostic kit can also be used for obtaining data for adjusting or determining a plan of examination for predicting the onset of an adverse event due to administration of at least one antibody drug selected from an anti-PD-1 antibody, an anti-PD-L1 antibody, an anti-CTLA4 antibody, and an antigen-binding fragment thereof as mentioned later.

According to another embodiment of the present invention, a method of measuring a level of at least one marker selected from sCD163 and CXCL5 in a biological sample collected from a subject administered at least one antibody drug selected from an anti-PD-1 antibody, an anti-PD-L1 antibody, an anti-CTLA4 antibody, and an antigen-binding fragment thereof and, based on the obtained result of prediction of the onset of an adverse event, for preventing, suppressing, or delaying the onset of the adverse event, for keeping the grade or irAE evaluation of the adverse event occurred low, or for improving the adverse event occurred is provided. Here, the low grade or irAE evaluation of an adverse event is preferably 1 to 2. Examples of the method of preventing, suppressing, or delaying the onset of the adverse event, the method of keeping the grade or irAE evaluation of the adverse event occurred low, or the method of improving the adverse event occurred as mentioned above include administration of an effective dose of a drug or reduction of the dose of the above-mentioned antibody drug administered or discontinuation or interruption of administration of the above-mentioned antibody drug. As the drug to be administered, a drug useful for an adverse event whose onset was predicted or that occurred is selected. For example, when the adverse event is an immune-related adverse event, a steroid such as adrenocortical hormone or an immunosuppressive agent is exemplified, and specific examples of the steroid include cortisol (hydrocortisone, cortisone), prednisolone (methylprednisolone, prednisolone), triamcinolone, dexamethasone, betamethasone, or a salt thereof. Examples of the drug to be administered include preferably an intermediate-acting steroid with a half-life in blood of about 3 hours and a biological half-life of 12 to 36 hours, and more preferably methylprednisolone or prednisolone. According to any of another preferred embodiment mentioned above, a method of measuring a level of at least one marker selected from sCD163 and CXCL5 in a biological sample collected from a subject administered at least one antibody drug selected from an anti-PD-1 antibody, an anti-PD-L1 antibody, an anti-CTLA4 antibody, and an antigen-binding fragment thereof, and based on the result of prediction of the onset of an adverse event, of using the result for judgment of whether prophylactic administration of a drug is performed or not is included.

Therefore, according to another preferred embodiment of the present invention, a method of measuring a level of at least one marker selected from sCD163 and CXCL5 in a biological sample collected from a subject administered at least one antibody drug selected from an anti-PD-1 antibody, an anti-PD-L1 antibody, an anti-CTLA4 antibody, and an antigen-binding fragment thereof, and based on the obtained result of prediction of the onset of an adverse event, of preventing, suppressing, or delaying the onset of the adverse event, of keeping the grade or irAE evaluation of the adverse event occurred low, or of improving the adverse event occurred, comprising a step of administering an effective dose of a drug to a subject requiring it is provided.

According to another preferred embodiment of the present invention, a method of confirming the effect of a drug administered, comprising measuring a level of at least one marker selected from sCD163 and CXCL5 in a biological sample collected from a subject administered the above-mentioned drug, is provided. The method of confirming the effect of the above-mentioned drug can be performed according to a description on the method of predicting the onset of an adverse events. When a level difference or level ratio of a marker is used to confirm the effect of a drug, a level of the above-mentioned marker in a biological sample from a subject after administration of the above-mentioned drug and a level of the above-mentioned marker in a biological sample collected from a subject before administration of the above-mentioned antibody drug may be used in a subject in whom the effect of the drug is confirmed. Examples of after administration of the above-mentioned drug include within 12 weeks, preferably within 9 weeks, and more preferably within 6 weeks after administration of the above-mentioned drug. Examples of the effect of the above-mentioned drug include preventing, suppressing, or delaying the onset of an adverse event, keeping the grade or irAE evaluation of the adverse event occurred low, or improving the adverse event occurred.

The effective dose of the above-mentioned drug is not particularly limited, and appropriately determined by a person skilled in the art according to the type or purity of the drug, the type or severity of the adverse event, the type, disposition, sex, age, or symptom of the subject or the like. Examples of the effective dose include 0.1 to 20 mg/body weight kg/day and preferably 1.0 to 20 mg/body weight kg/day once or several times.

The subjects of the present invention are mammals, example, rodents, dogs, cats, cattle, primates or the like, preferably humans, more preferably humans suffering from cancer, sarcoma, or malignant mesothelioma. The subjects may be humans who administered a drug and preferably a steroid.

According to another embodiment of the present invention, a method of assisting in predicting the onset of an adverse event due to administration of at least one antibody drug selected from an anti-PD-1 antibody, an anti-PD-L1 antibody, an anti-CTLA4 antibody, and an antigen-binding fragment thereof, comprising measuring a level of at least one marker selected from sCD163 and CXCL5 in a biological sample collected from a subject administered the above-mentioned antibody drug, is provided.

According to another embodiment of the present invention, a method of diagnosing the onset of an adverse event due to administration of at least one antibody drug selected from an anti-PD-1 antibody, an anti-PD-L1 antibody, an anti-CTLA4 antibody, and an antigen-binding fragment thereof, comprising measuring a level of at least one marker selected from sCD163 and CXCL5 in a biological sample collected from a subject administered the above-mentioned antibody drug, is provided.

According to another embodiment of the present invention, a method of assisting in diagnosing the onset of an adverse event due to administration of at least one antibody drug selected from an anti-PD-1 antibody, an anti-PD-L1 antibody, an anti-CTLA4 antibody, and an antigen-binding fragment thereof, comprising measuring a level of at least one marker selected from sCD163 and CXCL5 in a biological sample collected from a subject administered the above-mentioned antibody drug, is provided.

According to another embodiment of the present invention, use of sCD163 or CXCL5, in a subject administered at least one antibody drug selected from an anti-PD-1 antibody, an anti-PD-L1 antibody, an anti-CTLA4 antibody, and an antigen-binding fragment thereof, as a marker for predicting the onset of an adverse event due to administration of the antibody drug is provided. The above-mentioned sCD163 or CXCL5 is preferably included in a biological sample collected from the above-mentioned subject.

According to another embodiment of the present invention, use of sCD163 or CXCL5 in the manufacture of a marker for, in a subject administered at least one antibody drug selected from an anti-PD-1 antibody, an anti-PD-L1 antibody, an anti-CTLA4 antibody, and an antigen-binding fragment thereof, predicting the onset of an adverse event due to administration of the antibody drug is provided.

According to another embodiment of the present invention, a method of obtaining data for adjusting or determining a plan of examination for predicting the onset of an adverse event due to administration of at least one antibody drug selected from an anti-PD-1 antibody, an anti-PD-L1 antibody, an anti-CTLA4 antibody, and an antigen-binding fragment thereof, comprising measuring a level of at least one marker selected from sCD163 and CXCL5 in a biological sample collected from a subject administered the above-mentioned antibody drug, is provided. Usually, clinical examination has been performed every 2 to 3 weeks, which are dosing intervals of the above-mentioned antibody drug. When the above-mentioned method predicts that the possibility of the onset of an adverse event is high based on the obtained data, the dosing interval can be changed to a shorter interval than usual, for example, every 1 week to twice weekly. Furthermore, clinical examination items can be changed from usual clinical examination items in association with prediction that the possibility of the onset of an adverse event is high.

The above-mentioned usual clinical examination items are exemplified below.

Protocol Treatment: Week 0 (Before Administration)
  Physical findings: ECOG, PS
  Skin findings: Presence or absence, size, and number of skin metastatic lesions
  Blood test (blood count): red blood cell, white blood cell, platelet, hemoglobin level, hematocrit, differential white blood count
  Biochemical test: AST, ALT, γ-GTP, ALP, LDH, total bilirubin, BUN, creatinine, CK, TSH, T3, T4, KL6, cortisol
  Combination treatment and supportive therapy: The contents of the combination therapy and supportive therapy performed during the protocol treatment are recorded.
  Subjective and objective findings: The grade of the following items is judged using CTCAE v4.0-JCOG.
Gastrointestinal disorders, skin and subcutaneous tissue disorders, psychiatric disorders, respiratory, thoracic and mediastinal disorders Protocol Treatment: Week 3
  Physical findings: ECOG PS
  Skin findings: Presence or absence, size, and number of skin metastatic lesions
  Blood test (blood count): Red blood cell, white blood cell, platelet, hemoglobin level, hematocrit, differential white blood count
  Biochemical test: AST, ALT, γ-GTP, ALP, LDH, total bilirubin, BUN, creatinine, CK, TSH, T3, T4, KL6, cortisol
  Combination treatment and supportive therapy: The contents of the combination therapy and supportive therapy performed during the protocol treatment are recorded,
  Subjective and objective findings: The grade of the following items is judged using CTCAE v4.0-JCOG.
Gastrointestinal disorders, skin and subcutaneous tissue disorders, psychiatric disorders, respiratory, thoracic and mediastinal disorders At the End of Protocol Treatment (Week 6)
  Physical findings: ECOG, PS
  Skin findings: Presence or absence, size, and number of skin metastatic lesions
  Blood test (blood count) Red blood cell, white blood cell, platelet, hemoglobin level, hematocrit, differential white blood count
  Biochemical test: AST, ALT, γ-GTP, ALP, LDH, total bilirubin, BUN, creatinine, CK, TSH, T3, T4, KL6, cortisol
  Chest CT: Presence or absence of interstitial pneumonia and presence or absence of pleural effusion are verified.
  Subjective and objective findings: The grade of the following items is judged using CTCAE v4.0-JCOG.
Gastrointestinal disorders, skin and subcutaneous tissue disorders, psychiatric disorders, respiratory, thoracic and mediastinal disorders Clinical examination items to be measured in a short interval "in the case of prediction that the possibility of the onset of an adverse event is high" as mentioned above are exemplified.

Peripheral blood, differential white blood count, CRP

Any embodiments of the method of preventing, suppressing, or delaying the onset of an adverse event, the method of keeping the grade or irAE evaluation of the adverse event occurred low, the method of improving the adverse event occurred, the method of assisting in predicting the onset of an adverse event, the method of diagnosing the onset of an adverse event, the method of assisting in diagnosing the onset of an adverse event, the use as a marker, the use for the manufacture of a marker, and the method of obtaining data for determining a plan of examination for predicting the onset of an adverse event as mentioned above can be performed by the same method as the method of obtaining data and the method of predicting the onset of an adverse event.

EXAMPLES

The present invention will be specifically described below by way of Examples, but the technical scope of the present invention is not limited to these Examples, Unless otherwise mentioned, the units and the measurement methods as mentioned herein are in conformity with JIS standards.

Test Example 1: Measurement of scD163 and CXCL5 in Serum of Patient Before and after Administration of Nivolumab Subjects were 8 patients suffering from malignant melanoma administered nivolumab. No adverse event due to administration of nivolumab was observed in 7 of 8 patients administered nivolumab. On the other hand, an adverse event due to administration of nivolumab was observed in 1 patient. The patient with the adverse event had a melanoma metastatic lesion and was administered 2 mg/kg of nivolumab once every 3 weeks. Six months after administration of nivolumab, the patient was examined by MRI for brain metastasis and by CT scan for systemic metastasis, and as a result, brain metastasis was diagnosed. During the same period, a thyroid-stimulating hormone (TSH) level began to increase (2.84 μIU/mL), a serum TSH level was observed to be 7.07 μIU/mL 8 months after administration of nivolumab, and the above-mentioned patient was suspected to suffer from hypopituitarism. Therefore, a corticotropin-releasing hormone (CRH) challenge test was performed for the above-mentioned patient and showed decrease in serum adrenocorticotropic hormone (ACTH) (less than 1.0 ng/mL) and decrease in cortisol (0.8 μg/dL), and thus the above-mentioned patient was diagnosed with ACTH deficiency.

For the 8 patients mentioned above, serum before administration and 6 weeks after administration of nivolumab was collected, and the serum sCD163 and CXCL5 concentrations were measured by ELISA. Specifically, the measurement of the serum sCD163 concentration was performed using a kit comprising an antibody that specifically binds to sCD163, Human CD163 DuoSet (catalog number: DY1607) (R and D system, Minneapolis, Minn.), in accordance with the protocol. The measurement of the serum CXCL5 concentration was performed using Human CXCL5/ENA-78 DuoSet ELISA (catalog number: DY254) (R and D system, Minneapolis, Minn.), in accordance with the protocol.

Also, with respect to TNFα concentration, serum before administration and 6 weeks after administration of nivolumab was collected, and the serum. TNFα concentration was measured by ELISA. Specifically, the measurement of the serum TNFα concentration was performed using Human TNFa DuoSet (catalog number: DY210) (R and D system, Minneapolis, Minn.), in accordance with the protocol.

Figure 1B:
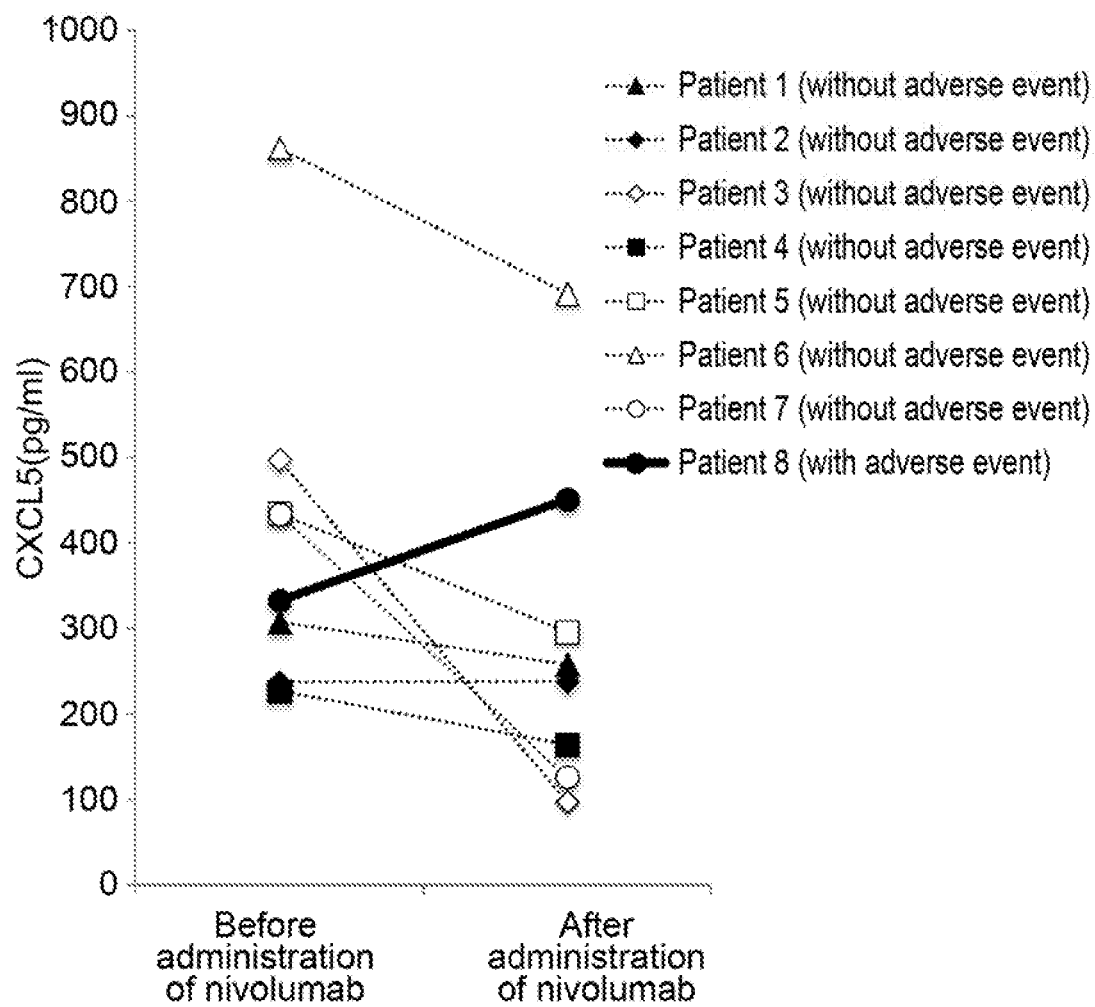

As shown in FIGS. 1A and 1B, the serum sCD163 and CXCL5 concentrations were upregulated in 1 patient with an adverse event due to administration of nivolumab compared with 7 patients without adverse event due to administration of nivolumab (in the case of sample number n=3, paired t-test, significant difference for p<0.05).

TNFα was not detected in any patients.

Test Example 2: Measurement of sCD163 and CXCL5 in Serum in Patient Before and after Administration of Nivolumab (46 Cases)

Like Test Example 1, subjects were 46 patients suffering from malignant melanoma administered nivolumab. Specifically, 2 mg/kg of nivolumab was administered once every 3 weeks or 3 mg/kg of nivolumab was administered once every 2 weeks to patients 1 to 46. For the 46 patients mentioned above, serum before administration and 6 weeks after administration of nivolumab was collected, and the serum sCD163 and CXCL5 concentrations were measured by ELISA. Of the 46 patients mentioned above, patients 1 to 8 are the same patients as the patients in Test Example 1, and the patients were continuously examined after Test Example 1.

The results are shown in Table 1.

TABLE 1

| | CXCL5 concentration | | | | sCD163 concentration | | | | | |
|---|---|---|---|---|---|---|---|---|---|---|
| Patient | Before administration (pg/ml) | 6 weeks after administration (pg/ml) | Fluctuation value (pg/ml) | Fluctuation ratio (%) | Before administration (ng/ml) | 6 weeks after administration (ng/ml) | Fluctuation value (ng/ml) | Fluctuation ratio (%) | irAE diagnosis | irAE evaluation |
| 1 | 307.7 | 257.9 | −49.7 | −16.2% | 21.0 | 22.5 | 1.6 | 7.5% | — | 0 |
| 2 | 237.6 | 238.2 | 0.6 | 0.3% | 55.1 | 45.4 | −9.7 | −17.6% | — | 0 |
| 3 | 497.5 | 97.4 | −400.1 | −80.4% | 49.7 | 31.9 | −17.8 | −35.8% | — | 0 |
| 4 | 226.9 | 164.2 | −62.7 | −27.6% | 23.6 | 35.1 | 11.6 | 49.0% | Bursitis | 2 |
| 5 | 434.8 | 295.7 | −139.0 | −32.0% | 24.0 | 36.7 | 12.7 | 52.7% | Remarkable exacerbation of radiodermatitis | 3 |
| 6 | 862.1 | 691.8 | −170.3 | −19.8% | 82.5 | 70.4 | −12.1 | −14.7% | — | 0 |
| 7 | 434.0 | 126.1 | −307.9 | −70.9% | 85.9 | 76.9 | −9.0 | −10.5% | Thyroid dysfunction | 1 |
| 8 | 332.6 | 450.9 | 118.3 | 35.6% | 39.8 | 90.6 | 50.9 | 127.8% | Hypophysitis | 3 |
| 9 | 461.4 | 377.3 | −84.0 | −18.2% | 27.7 | 28.7 | 1.0 | 3.6% | — | 0 |
| 10 | 314.9 | 308.0 | −6.9 | −2.2% | 40.0 | 46.7 | 6.8 | 16.9% | — | 0 |
| 11 | 509.4 | 541.3 | 31.9 | 6.3% | 28.7 | 42.0 | 13.3 | 46.2% | Hypophysitis | 1 |
| 12 | 416.9 | 314.0 | −102.9 | −24.7% | 26.6 | 33.8 | 7.2 | 27.0% | — | 0 |
| 13 | 423.4 | 433.8 | 10.4 | 2.5% | 28.9 | 32.9 | 4.0 | 13.9% | — | 0 |
| 14 | 471.9 | 478.6 | 6.7 | 1.4% | 50.6 | 45.5 | −5.1 | −10.1% | — | 0 |
| 15 | 535.7 | 441.5 | −94.2 | −17.6% | 52.1 | 35.3 | −16.8 | −32.2% | Hepatic disorder | 3 |
| 16 | 414.3 | 370.0 | −44.2 | −10.7% | 15.0 | 16.1 | 1.1 | 7.3% | — | 0 |
| 17 | 226.8 | 133.9 | −92.9 | −41.0% | 17.6 | 20.3 | 2.7 | 15.4% | — | 0 |
| 18 | 238.4 | 230.3 | −8.1 | −3.4% | 18.8 | 19.4 | 0.7 | 3.5% | Thyroid dysfunction | 1 |
| 19 | 416.7 | 307.9 | −108.7 | −26.1% | 29.4 | 29.3 | −0.1 | −0.3% | — | 0 |
| 20 | 405.3 | 409.7 | 4.5 | 1.1% | 25.3 | 31.1 | 5.8 | 23.1% | — | 0 |
| 21 | 406.9 | 1115.2 | 708.4 | 174.1% | 33.7 | 33.9 | 0.2 | 0.5% | Pulmonary disorder | 3 |
| 22 | 222.6 | 229.1 | 6.5 | 2.9% | 95.6 | 34.0 | −61.6 | −64.5% | Thyroid dysfunction | 1 |
| 23 | 667.8 | 836.1 | 168.3 | 25.2% | 82.3 | 64.8 | −17.5 | −21.3% | Thyroid dysfunction | 1 |
| 24 | 502.8 | 227.2 | −275.6 | −54.8% | 64.3 | 85.8 | 21.5 | 33.4% | Psoriasiform rash | 2 |
| 25 | 408.6 | 469.6 | 61.0 | 14.9% | 70.7 | 57.7 | −13.0 | −18.4% | — | 0 |
| 26 | 940.0 | 83.0 | −857.1 | −91.2% | 48.7 | 42.2 | −6.5 | −13.4% | Inflammatory demyelinating polyneuropathy | 3 |
| 27 | 332.5 | 978.0 | 645.5 | 194.1% | 33.3 | 35.8 | 2.5 | 7.6% | — | 0 |
| 28 | 162.9 | 138.0 | −24.9 | −15.3% | 52.4 | 69.4 | 17.1 | 32.6% | Psoriasiform rash | 2 |
| 29 | 333.6 | 329.7 | −3.9 | −1.2% | 114.9 | 290.5 | 175.6 | 152.9% | Autoimmune pneumonia | 2 |
| 30 | 271.6 | 198.8 | −72.8 | −26.8% | 27.2 | 30.3 | 3.1 | 11.3% | — | 0 |
| 31 | 381.0 | 551.6 | 170.7 | 44.8% | 53.7 | 62.0 | 8.3 | 15.4% | — | 0 |
| 32 | 237.4 | 316.7 | 79.3 | 33.4% | 33.8 | 53.4 | 19.6 | 58.2% | — | 0 |
| 33 | 5026.4 | 3880.6 | −1145.8 | −22.8% | 36.7 | 57.0 | 20.3 | 55.2% | Rheumatoid arthritis | 3 |
| 34 | 474.3 | 964.4 | 490.1 | 103.3% | 42.9 | 60.3 | 17.3 | 40.4% | Hypophysitis | 1 |
| 35 | 494.1 | 459.0 | −35.1 | −7.1% | 22.7 | 21.1 | −1.6 | −7.0% | — | 0 |
| 36 | 370.5 | 311.7 | −58.8 | −15.9% | 34.2 | 39.7 | 5.5 | 15.9% | Diarrhea | 2 |
| 37 | 501.8 | 658.9 | 157.1 | 31.3% | 27.3 | 14.7 | −12.6 | −46.3% | — | 0 |
| 38 | 407.0 | 408.9 | 1.9 | 0.5% | 27.4 | 51.9 | 24.5 | 89.5% | Hypophysitis | 1 |
| 39 | 223.6 | 244.8 | 21.2 | 9.5% | 45.5 | 43.8 | −1.7 | −3.8% | — | 0 |
| 40 | 572.8 | 688.9 | 116.1 | 20.3% | 19.3 | 23.2 | 3.9 | 20.1% | — | 0 |
| 41 | 535.0 | 866.2 | 331.2 | 61.9% | 42.2 | 38.8 | −3.3 | −7.9% | Biliary tract disorder | 3 |
| 42 | 409.6 | 308.9 | −100.8 | −24.6% | 25.0 | 17.6 | −7.4 | −29.5% | Adrenal insufficiency | 1 |

TABLE 1-continued

| | CXCL5 concentration | | | | sCD163 concentration | | | | | |
|---|---|---|---|---|---|---|---|---|---|---|
| Patient | Before administration (pg/ml) | 6 weeks after administration (pg/ml) | Fluctuation value (pg/ml) | Fluctuation ratio (%) | Before administration (ng/ml) | 6 weeks after administration (ng/ml) | Fluctuation value (ng/ml) | Fluctuation ratio (%) | irAE diagnosis | irAE evaluation |
| 43 | 504.4 | 366.6 | −137.8 | −27.3% | 16.0 | 11.1 | −4.9 | −30.7% | — | 0 |
| 44 | 698.2 | 619.0 | −79.3 | −11.4% | 11.4 | 7.3 | −4.1 | −36.0% | Adrenal insufficiency | 1 |
| 45 | 687.0 | 354.5 | −332.5 | −48.4% | 15.5 | 11.7 | −3.8 | −24.4% | Adrenal insufficiency | 2 |
| 46 | 1966.7 | 1491.6 | −475.0 | −24.2% | 13.3 | 12.7 | −0.5 | −4.1% | — | 0 |

In patients 4, 5, and 7, no adverse event due to administration of nivolumab was observed at the time of examination in Test Example 1. Subsequent examination revealed the onset of adverse events shown in Table 1, 8 weeks after administration of nivolumab in patient 4, 60 weeks after administration of nivolumab in patient 5, and 16 weeks after administration of nivolumab in patient 7, Patient 8 showed the onset of hypophysitis 30 weeks after administration of nivolumab.

Using a cut-off value (threshold) predetermined based on the results of Table 1 mentioned above, a positive predictive value, a negative predictive value, and a predictive value were calculated in accordance with the following criteria.

Specifically, of patients who actually had an adverse event, the case where the possibility of the onset of an adverse event was also judged to be high in this test was considered "positive", and the case where the possibility of the onset of an adverse event was not judged to be high was considered "false-negative".

Of patients who actually had no adverse event, the case where the possibility of the onset of an adverse event was also not judged to be high in this test was considered "negative", and the case where the possibility of the onset of an adverse event was judged to be high was considered "false-positive".

The proportion of patients who actually had an adverse event, namely positive patients, in patients in whom the possibility of the onset of an adverse event was judged to be high in this test was considered as the positive predictive value.

The proportion of patients who actually had no adverse event, namely negative patients, in patients in whom the possibility of the onset of an adverse event was not judged to be high in this test was considered as the negative predictive value.

The proportion of patients in whom the possibility of the onset of an adverse event was judged to be high in this test in patients who actually had an adverse event was considered as the sensitivity.

The proportion of patients in whom the possibility of the onset of an adverse event was not judged to be high in this test in patients who actually had no adverse event was considered as the specificity.

The proportion of positive patients and negative patients to all patients was considered as the predictive value in this test.

With respect to the fluctuation ratio data on all 46 cases, the mean of sCD163 was 10.8% and the mean of CXCL5 was 0.0%. With respect to the fluctuation ratio data based on the mean, the standard deviation of sCD163 was 30.8% and the standard deviation of CXCL5 was 40.5%.

1. Setting of Threshold Based on Standard Deviation of sCD163 and CXCL5

The threshold was set as ±1 standard deviation ($\sigma$) based on the mean of the fluctuation ratio data on sCD163 and CXCL5. (threshold set: sCD163, upper limit of 42%, lower limit of −20%; CXCL5, upper limit of 41%, lower limit of −41%)

Here, patients in whom the fluctuation ratio of CXCL5 measured is the upper limit or more or lower limit or less of the above-mentioned threshold or the fluctuation ratio of sCD163 measured is the upper limit or more or lower limit or less of the above-mentioned threshold were considered as patients with a high possibility of the onset of an adverse event.

Based on the above-mentioned criteria, the predictive value and the like were calculated.

The results are shown in Table 2.

TABLE 2

| Positive | 19 |
|---|---|
| False-positive | 6 |
| Negative | 18 |
| False-negative | 3 |
| Positive predictive value (%) | 86.4% |
| Negative predictive value (%) | 75.0% |
| Sensitivity (%) | 86.4% |
| Specificity (%) | 75.0% |
| Predictive value (%) | 80.4% |

2. Setting of Threshold Based on ROC Curve of sCD163

Figure 2:
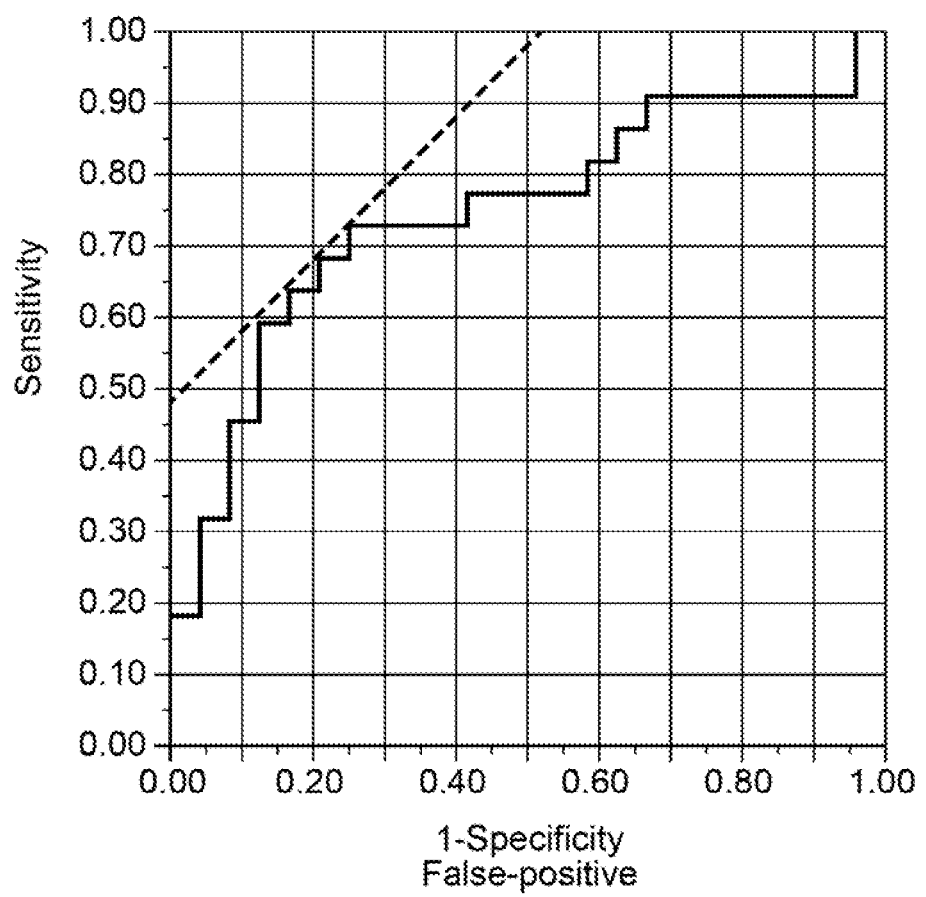
FIG. 2.

An ROC curve was prepared based on the absolute value of the difference between the fluctuation ratio data on sCD163 in 46 cases and the mean thereof. FIG. 2 shows the ROC curve.

The horizontal axis of the ROC curve represents (1−specificity), and this increases with the proportion of false-positive. The longitudinal axis represents sensitivity. In preparation, irAE=1 is considered "positive". The point where "sensitivity−(1−specificity)" is maximum in this ROC curve was 0.231, and the area under the ROC curve (AUC) was 0.746.

The threshold was set as the mean of sCD163±21.3%, (threshold set: sCD163, upper limit of 32%, lower limit of −11%)

Patients in whom the fluctuation ratio data of sCD163 measured is the upper limit or more or lower limit or less of the above-mentioned threshold were considered as patients with a high possibility of the onset of an adverse event.

Based on the above-mentioned criteria, the predictive value and the like were calculated.

The results are shown in Table 3,

TABLE 3

| | |
|---|---|
| Positive | 17 |
| False-positive | 7 |
| Negative | 17 |
| False-negative | 5 |
| Positive predictive value (%) | 70.8% |
| Negative predictive value (%) | 77.3% |
| Sensitivity (%) | 81.8% |
| Specificity (%) | 70.3% |
| Predictive value (%) | 73.9% |

3. Setting of Threshold Based on ROC Curve of sCD163 and CXCL5

Furthermore, in the same manner as for sCD163 mentioned in 2, an ROC curve was prepared based on the absolute value of the difference between the fluctuation ratio data on CXCL5 and the mean thereof, and the threshold of CXCL5 was also set.

(threshold set: sCD163, upper limit of 32%, lower limit of −11%; CXCL5, upper limit of 48%, lower limit of −48%)

Here, patients in whom the fluctuation ratio of CXCL5 measured is the upper limit or more or lower limit or less of the above-mentioned threshold or the fluctuation ratio of sCD163 measured is the upper limit or more or lower limit or less of the above-mentioned threshold were considered as patients with a high possibility of the onset of an adverse event.

Based on the above-mentioned criteria, the predictive value and the like were calculated.

As a result, the positive predictive value was 71.4%, the negative predictive value was 88.9%, the sensitivity was 90.9%, and the predictive value was 78.3%, which increased compared with the case of only sCD163 in 2 mentioned above. Meanwhile, the specificity was similar to that in the case of only sCD163 in 2 mentioned above.

4. Setting Using the Same Threshold Range for sCD163 and CXCL5

The threshold of sCD163 and CXCL5 was set as the mean±32%. (threshold: sCD163, upper limit of 43%, lower limit of −21%; CXCL5, upper limit of 32%, lower limit of −32%)

Here, patients in whom the fluctuation ratio of CXCL5 measured is the upper limit or more or lower limit or less of the above-mentioned threshold or the fluctuation ratio of sCD163 measured is the upper limit or more or lower limit or less of the above-mentioned threshold were considered as patients with a high possibility of the onset of an adverse event.

Based on the above-mentioned criteria, the predictive value and the like were calculated.

The results are shown in Table 4.

TABLE 4

| | |
|---|---|
| Positive | 19 |
| False-positive | 7 |
| Negative | 17 |
| False-negative | 3 |
| Positive predictive value (%) | 73.1 |
| Negative predictive value (%) | 85.0 |
| Sensitivity (%) | 86.4 |

TABLE 4-continued

| | |
|---|---|
| Specificity (%) | 70.8 |
| Predictive value (%) | 78.3 |

The invention claimed is:

1. A method of suppressing or delaying an onset of an adverse event or of improving the adverse event occurred in a subject due to administration of at least one antibody drug selected from an anti-PD-1 antibody, an anti-PD-L1 antibody, an anti-CTLA4 antibody, and an antigen-binding fragment thereof, the method comprising:
   measuring a level of at least one marker selected from sCD163 and CXCL5 in a biological sample collected from the subject before the antibody drug is administered,
   measuring a level of at least one marker selected from sCD163 and CXCL5 in a biological sample collected from the subject administered the antibody drug, and
   administering an effective dose of a drug selected from a steroid and an immunosuppressive agent to the subject when (i) the level of sCD163 collected from the subject administered the antibody drug is 1.2-fold or more higher than the level of sCD163 collected from the subject before the antibody drug is administered, (ii) a concentration of sCD163 collected from the subject administered the antibody drug is at least 10 ng/mL more than a concentration of sCD163 collected from the subject before the antibody drug is administered, (iii) the level of CXCL5 collected from the subject administered the antibody drug is 1.05-fold or more higher than the level of CXCL5 collected from the subject before the antibody drug is administered, or (iv) a concentration of CXCL5 collected from the subject administered the antibody drug is at least 50 pg/mL more than a concentration of CXCL5 collected from the subject before the antibody drug is administered.

2. The method according to claim 1, wherein the anti-PD-1 antibody is nivolumab.

3. The method according to claim 1, wherein the anti-CTLA4 antibody is ipilimumab.

4. The method according to claim 1, wherein the antibody drug is an anticancer agent.

5. The method according to claim 1, wherein the adverse event is an immune-related adverse event.

6. The method according to claim 1, wherein the marker is a combination of sCD163 and CXCL5.

7. The method according to claim 1, comprising obtaining comparative data between a level of the marker in a biological sample collected from a subject administered the antibody drug and a level of a corresponding marker in a biological sample collected from a subject before administration of the antibody drug.

8. The method according to claim 7, wherein the level of the marker in a biological sample collected from a subject administered the antibody drug or the comparative data serves as an index of an onset of an adverse event.

9. The method according to claim 7, wherein the level of the marker in a biological sample collected from a subject administered the antibody drug or the comparative data serves as an index of administration of a steroid to the subject.

10. The method according to claim 8, wherein the comparative data serves as an index of an onset of an adverse event.

* * * * *